United States Patent
Kidd et al.

(10) Patent No.: US 9,879,324 B2
(45) Date of Patent: Jan. 30, 2018

(54) GENETIC DETERMINANTS OF PROSTATE AND BREAST CANCER RISK

(75) Inventors: La Creis Renee Kidd, Louisville, KY (US); Kevin Sean Kimbro, Durham, NC (US)

(73) Assignees: University of Louisville Research Fondation, Inc., Louisville, KY (US); North Carolina Central University, Durham, NC (US)

( * ) Notice: Subject to any disclaimer, the term of this patent is extended or adjusted under 35 U.S.C. 154(b) by 668 days.

(21) Appl. No.: 14/009,197

(22) PCT Filed: Mar. 30, 2012

(86) PCT No.: PCT/US2012/031501
§ 371 (c)(1),
(2), (4) Date: Apr. 17, 2014

(87) PCT Pub. No.: WO2012/138566
PCT Pub. Date: Oct. 11, 2012

(65) Prior Publication Data
US 2014/0221226 A1 Aug. 7, 2014

Related U.S. Application Data

(60) Provisional application No. 61/471,636, filed on Apr. 4, 2011.

(51) Int. Cl.
*C12Q 1/68* (2006.01)
(52) U.S. Cl.
CPC ...... *C12Q 1/6886* (2013.01); *C12Q 2600/112* (2013.01); *C12Q 2600/118* (2013.01); *C12Q 2600/156* (2013.01); *C12Q 2600/172* (2013.01); *Y10T 436/143333* (2015.01)

(58) Field of Classification Search
None
See application file for complete search history.

(56) References Cited

PUBLICATIONS

Authorized officer Lee Hyun Ji, International Search Report/Written Opinion in PCT/US2012/031501 dated Jan. 3, 2013, 6 pages.
Luster et al., "Chemokines—Chemotactic Cytokines That Mediate Inflammation," The New England Journal of Medicine, Feb. 1998, 338:436-45.
Maniatis et al., "The first linkage disequilibrium (LD) maps: Delineation of hot and cold blocks by diplotype analysis," PNAS, Feb. 2002, 99:2228-2233.
Morton et al., "The optimal measure of allelic association," PNAS, 2001, 98(9):5217-21.
Odedina et al., "Prostate cancer disparities in Black men of African descent: a comparative literature review of prostate cancer burden among Black men in the United States, Caribbean, United Kingdom, and West Africa," Infect. Agents Can., 2009, 4(Suppl 1):S2, 1-8.
Rollins et al., "Chemokines," Blood, 1997, 90:909-28.
Strieter et al., "CXC chemokines in angiogenesis," Cytokine & Growth Factor Reviews, Dec. 2005, 16(6):593-609.
Strieter et al., "The Functional Role of the ELR Motif in CXC Chemokine-mediated Angiogenesis," The Journal of Biological Chemistry, Nov. 1995, 270:27348-57.
Tapper et al., "A map of the human genome in linkage disequilibrium units," PNAS, 2005, 102(33):11835-11839.
The International HapMap Consortium, Nature, 2003, 426:789-796.
The International HapMap Consortium, Nature, 2005, 437:1299-1320.

*Primary Examiner* — Jehanne S Sitton
(74) *Attorney, Agent, or Firm* — Fish & Richardson P.C.

(57) ABSTRACT

Described are methods of determining if a subject has a genetic predisposition to developing prostate cancer (PCa) or aggressive PCa, or to developing breast cancer (BrCa).

11 Claims, 1 Drawing Sheet

| dbSNP ID | Sequence [major/minor allele] | SEQ ID NO: |
|---|---|---|
| rs10491121 | CTAGCCCTATCCCCTTCCTGAATTAAGTCC[G/A]AATATAGTCAGTCTTTGAGTGTGGAATAGC | 1. |
| rs12107527 | GGCTCACCATTGATCTTTGCTTATCACATA[C/T]AAAACTCTCATAAAGGAACTGGGTTTTCCC | 2. |
| rs14304 | GGCATAGCAGATGGGACTCTTAGAAGAGGT[G/A]GCCTCCAGGGTGGCAGGGCCATTGCCCTGG | 3. |
| rs16951657 | TTCATAGTAGGTATGCATATGTTTGTTTCT[G/T]TACAGTACTGTGTGTGTGTGTGTATATA | 4. |
| rs1719147 | GGGCCTGTTTTGGGGAGGGGGTGATTGAGC[G/A]TTGGGGAGGCAGCTCCCAGGGCTGAAGCCT | 5. |
| rs2063979 | CTAGGGGTAAACTCTTAGTCCAAAACCCAA[A/G]CATGCAATAAATAAAACTCCCTTATTTGAC | 6. |
| rs2069716 | TTGAGGCATAAAGACAAATCATGTTTTTCA[A/G]AATGTTTTCTAGAAGACAAAGGCCTCTAGA | 7. |
| rs2228428 | CTGCCAATACTGTGGGCTCCTCCAAATTTA[C/T]TCTGCTGACACCCCAGCTCATCTTACACG | 8. |
| rs223895 | AGGCTCAGTGAGAGCACCTTTCCTAGAGCA[C/T]CAGAGCTGGAAGCCACATTGCTGAGGATTA | 9. |
| rs2284553 | TCAGGCAGGGCTCAGAACTGTCCGGGTCCC[G/A]TCAGTGTTGGGGCGGAAGAGGAAGAGTGTC | 10. |
| rs2300295 | GAGCATTCAGTAGGTATTTCTTAAGGATTA[C/A]TTTTTCCTATGACTGGAGTGAATCTGTCGA | 11. |
| rs2304973 | CCTGGGAATGGGTGCCGACCACCTCCGTCC[C/T]GCGCAGGCAATGGCAACGAGGGCAGCGTCA | 12. |
| rs2812377 | TTCCCCTCCTTCCAGCAAATCTGATTATTA[A/C]ATTGTAAGAGTTCTTTTTTTTTTTTTTT | 13. |
| rs3799488 | TAAAGTAGCACTTCTTACCACAGAGATCTC[C/T]GGGGAGAAAAATTGATTAAAGATAAAAAAT | 14. |
| rs4151117 | CAGGAGGCCAGCCTTGACCATTCTCCACCT[T/G]CCAGGGACAGAGGGGGTGGCCTCCCAACTC | 15. |
| rs6770096 | ATTGAGCCAGATGTATGAAGAAACAATTAG[C/T]GAAGTGATGAAACCAGATCTCAATTATTTA | 16. |
| rs779850 | ATGTCACAAATCCTGCTGGCTCTACATATA[C/T]AGTATTTCCGTATCCAGATAAATTGAAACT | 17. |
| rs8131980 | CTTGATCCTCCAAAGGTTATAAAGAAGGCC[G/A]GGGCCTAGTGCAGTGGCCCACGCCTATAAT | 18. |
| rs854656 | CTAATTCATTAATAAGTATTTTTGGCCCTA[A/C]TTCCAAAAATATAGCCAGAATCTTATTATT | 19. |
| rs854680 | TTTTTTGGAGTATTAGCATACACTGTGACA[G/T]GAAAGAGTGTGAGCTCAATCATGTGGCCTT | 20. |
| rs1876444 | GATGAAGATGATGGCCAGGAGGCACAGGAC[C/T]GGCACTGTGGCTGATGTCCTGGCTGTGGGA | 21. |
| rs3138036 | GCCCCTCTACCCCATAGAGAAACTCAGTCC [A/G]TGAGAAGGAGTCCATAACTGCTCTAGGATT | 22. |
| rs2023305 | CCACAAAAGAAGGCATACCCTAAGCATAAA [A/G]GAGAAATTCCACCCTCAAAATACTCATGTT | 23. |

SEQUENCE LISTING

<160> NUMBER OF SEQ ID NOS: 23

<210> SEQ ID NO 1
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = G or A

<400> SEQUENCE: 1
ctagccctat cccttcctg aattaagtcc naatatagtc agtctttgag tgtggaatag    60
c                                                                  61

<210> SEQ ID NO 2
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = C or T

<400> SEQUENCE: 2
ggctcaccat tgatctttgc ttatcacata naaaactctc ataaaggaac tgggttttcc    60
c                                                                  61

<210> SEQ ID NO 3
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = G or A

<400> SEQUENCE: 3
ggcatagcag atgggactct tagaagaggt ngcctccagg gtggcagggc cattgccctg    60
g                                                                  61

<210> SEQ ID NO 4
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = G or T

<400> SEQUENCE: 4
ttcatagtag gtatgcatat gtttgtttct ntacagtact gtgtgtgtgt gtgtgtatat    60
a                                                                  61

<210> SEQ ID NO 5
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = G or A

<400> SEQUENCE: 5
gggcctgttt tggggagggg gtgattgagc nttggggagg cagctcccag ggctgaagcc    60
t                                                                   61

<210> SEQ ID NO 6
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n =  A or G

<400> SEQUENCE: 6 ctagggtaa actcttagtc caaaacccaa ncatgcaata aataaaactc ccttatttga    60
c                                                                   61

<210> SEQ ID NO 7
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = A or G

<400> SEQUENCE: 7
ttgaggcata aagacaaatc atgtttttca naatgttttc tagaagacaa aggcctctag    60
a                                                                   61

<210> SEQ ID NO 8
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = C or T

<400> SEQUENCE: 8
ctgccaatac tgtgggctcc tccaaattta ntctgctgac accccagct catcttacac    60 g                                                                   61

<210> SEQ ID NO 9
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = C or T

<400> SEQUENCE: 9
aggctcagtg agagcaccttt tcctagagca ncagagctgg aagccacatt gctgaggatt    60
a                                                                    61

<210> SEQ ID NO 10
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = G or A

<400> SEQUENCE: 10
tcaggcaggg ctcagaactg tccgggtccc ntcagtgttg gggcggaaga ggaagagtgt    60
c                                                                    61

<210> SEQ ID NO 11
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = C or A

<400> SEQUENCE: 11
gagcattcag taggtatttc ttaaggatta nttttccta tgactggagt gaatctgtcg    60
a                                                                    61

<210> SEQ ID NO 12
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = C or T

<400> SEQUENCE: 12
cctgggaatg ggtgccgacc acctccgtcc ngcgcaggca atggcaacga gggcagcgtc    60
a                                                                    61

<210> SEQ ID NO 13
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = A or C

<400> SEQUENCE: 13
ttcccctcct tccagcaaat ctgattatta nattgtaaga gttctttttt tttttttttt    60
t                                                                    61

```
<210> SEQ ID NO 14
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = C or T

<400> SEQUENCE: 14
taaagtagca cttcttacca cagagatcta ngggggagaaa aattgattaa agataaaaaa    60
t                                                                    61

<210> SEQ ID NO 15
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = T or G

<400> SEQUENCE: 15
caggaggcca gccttgacca ttctccacct nccagggaca gaggggtgg cctcccaact      60 c                                                                    61

<210> SEQ ID NO 16
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = C or T

<400> SEQUENCE: 16
attgagccag atgtatgaag aaacaattag ngaagtgatg aaaccagatc tcaattattt     60
a                                                                    61

<210> SEQ ID NO 17
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = C or T

<400> SEQUENCE: 17
atgtcacaaa tcctgctggc tctacatata nagtatttcc gtatccagat aaattgaaac     60
t                                                                    61

<210> SEQ ID NO 18
<211> LENGTH: 61
<212> TYPE: DNA
<213> ORGANISM: Artificial Sequence
<220> FEATURE:
<223> OTHER INFORMATION: fragments of human genomic DNa
```

```
<220> FEATURE:
<221> NAME/KEY: misc_feature
<222> LOCATION: 31
<223> OTHER INFORMATION: n = G or A

<400> SEQUENCE: 18
cttgatcctc caaaggttat aaagaaggcc ngggcctagt gcagtggccc acgcctataa    60
t                                                                   61

<210> SEQ ID NO 19
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = A or C

<400> SEQUENCE: 19
ctaattcatt aataagtatt tttggcccta nttccaaaaa tatagccaga atcttattat    60
t                                                                   61

<210> SEQ ID NO 20
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = G or T

<400> SEQUENCE: 20 tttttttggag tattagcata cactgtgaca ngaaagagtg tgagctcaat catgtggcct    60
t                                                                   61

<210> SEQ ID NO 21
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = C or T

<400> SEQUENCE: 21
gatgaagatg atggccagga ggcacaggac nggcactgtg gctgatgtcc tggctgtggg    60
a                                                                   61

<210> SEQ ID NO 22
<211> LENGTH: 61
<212> TYPE: DNA
<213> ORGANISM: Artificial Sequence
<220> FEATURE:
<223> OTHER INFORMATION: fragments of human genomic DNA
<220> FEATURE:
<221> NAME/KEY: misc_feature
<222> LOCATION: 31
<223> OTHER INFORMATION: n = A or G
```

-continued

```
<400> SEQUENCE: 22
gcccctctac cccatagaga aactcagtcc ntgagaagga gtccataact gctctaggat    60
t                                                                   61

<210> SEQ ID NO 23
<211> LENGTH: 61
<212> TYPE: DNA
<213> ORGANISM: Artificial Sequence
<220> FEATURE:
<223> OTHER INFORMATION: fragments of human genomic DNa
<220> FEATURE:
<221> NAME/KEY: misc_feature
<222> LOCATION: 31
<223> OTHER INFORMATION: n = A or G

<400> SEQUENCE: 23
ccacaaaaga aggcataccc taagcataaa ngagaaattc caccctcaaa atactcatgt    60
t                                                                   61
```

US 9,879,324 B2

GENETIC DETERMINANTS OF PROSTATE AND BREAST CANCER RISK

CLAIM OF PRIORITY

This application claims the benefit of U.S. Provisional Patent Application Ser. No. 61/471,636, filed Apr. 4, 2011. The entire contents of the foregoing are incorporated by reference herein.

FEDERALLY SPONSORED RESEARCH OR DEVELOPMENT

This invention was made with Government support under Grant No. P20-MD000175 awarded by the National Institutes of Health. The Government has certain rights in the invention.

TECHNICAL FIELD

This invention relates to methods for predicting risk of developing prostate cancer, aggressive prostate cancer, or breast cancer, using genetic variants in chemokines/chemokine receptors including chemokine (C-C motif) ligand 161 (CCL16), chemokine (C-C motif) receptor 4 (CCR4), chemokine (C-X3-C motif) ligand 1 (CX3CL1), chemokine (C-C motif) ligand 17 (CCL17), protein inhibitor of activated STAT, 1 (PIAS1), chemokine (C-C motif) ligand 21 (CCL21), interferon gamma receptor 2 (interferon gamma transducer 1) (IFNGR2), chemokine (C-C motif) ligand 18 (CCL18) or chemokine (C motif) ligand 1 (XCL1) genes.

BACKGROUND

Recent studies have revealed participation of chemokines (e.g., CC, CXC, XCL, and C-X3-C gene families) in cancer by regulating leukocyte movement to modify local immunoresponse. Chemokines have multifaceted roles: they attract cancer cells and chemokine receptor bearing cells, especially T and dendritic cells; they facilitate dendritic cell functions; and they exert an angiostatic effect. Chemokines play a pivotal role in chemotaxis, leukocyte trafficking, lymphocyte development, angiogenesis, host response to infection, inflammatory processes, as well as tumor development, migration and metastasis. Chemokines mediate their actions through 7-transmembrane, G protein coupled receptors and serve three major physiological functions. First, they play fundamental roles in the maturation, homeostasis and function of the immune system, and facilitate the trafficking of memory T cells, lymphocytes, monocytes, and neutrophils to the inflammatory site. Secondly, they display chemotactic activity for lymphocytes, monocytes, and neutrophils. Lastly, they attract cancer cells and chemokine receptor bearing cells and have effects on endothelial cells involved in angiogenesis regulation. Several CXC chemokines are potent angiogenesis promoters (i.e., CXCL1, 2, 3, 5, 6, 7) (Luster et al., (1998) The New England Journal of Medicine, 338, 436-45; Rollins et al., (1997) Blood, 90, 909-28; Strieter et al., (2005) Cytokine & growth factor reviews, 16, 593-609); whereas, others inhibit angiogenesis (i.e., CXCL4, 9, 10, 11) (Strieter et al., (1995) The Journal of Biological Chemistry, 270, 27348-57).

SUMMARY

The present invention is based, at least in part, on the discovery that chemokine-related markers can be used as significant predictors of prostate cancer, aggressive prostate cancer, and breast cancer, e.g., among European-Americans. The inheritance of CCL16_rs2063979 "GG" (under the recessive genetic model), CCR4_rs2228428 "CT" or "CT+TT", CX3CL1_rs4151117 "GG", CCL17_rs223895 "TT", or PIAS1_rs16951657 "GT" or "GT+TT" was associated with an 1.25 to 1.56-fold increase in the risk of developing PCA ($p \leq 0.049$). In contrast, possession at least one minor CCL21_rs2812377 "C" allele or the IFNGR2_rs2284553 "AA" genotype was linked to a marginal 16 to 23% decrease in risk ($p \leq 0.041$). With respect to disease aggressiveness, inheritance the CCL4 rs1719147 "GA", CCL18_rs14304 "GA" or XCL1_rs2300295 "AA" genotypes were related to a 36-40% reduction in aggressive PCA ($p \leq 0.045$), relative to those with the referent genotype. In contrast, inheritance of the CCL16 rs854680 "TT", CCL16 rs2063979 "AG+GG", CCL28 rs779850 "TT", CCR4 rs6770096 "CT", IFNG rs2069716 "AG+GG" genotypes were linked to a 1.41-2.50 fold increase in the risk of developing aggressive prostate cancer.

In addition, possession of the CCL16_rs2063979 "GG" (under the recessive genetic model), CCL23 rs854656 "GG" (under the recessive genetic model), or IFNGR2 rs8131980 "GA+AA" genotypes was linked with a 21-37% reduction in BrCa risk after adjusting for age. Inheritance of the CCL17 rs223895 "CT+TT", CCR8 rs12107527 "TT" (under the recessive genetic model), or the CXCL16 rs2304973 "TT" (under the recessive genetic model) genotypes were associated with a 20-39% increase in the risk of developing BrCa.

Thus, the invention includes methods for determining a subject's risk of developing PCa or BrCa, or predicting disease aggressiveness or prognosis, based on detection of those allelic variants.

In one aspect, the invention includes methods for determining a subject's risk for developing PCa. The methods can include obtaining a sample comprising genomic DNA (gDNA) from the subject, and determining the identity, absence or presence of polymorphisms as described herein. In some embodiments, the methods include obtaining a test haplotype for the subject comprising polymorphisms of CCL16, CCR4, CX3CL1, CCL17, PIAS1, CCL21, IFNGR2, CCL18 and/or XCL1, wherein the haplotype provides information regarding the subject's risk of developing PCa. In some embodiments, the methods include determining the identity of one, two or more alleles selected from the group consisting of rs2063979, rs2228428, rs4151117, rs223895, rs16951657, rs2284553, and rs2812377 in the subject, e.g., in the sample from the subject. In some embodiments, the identities of both alleles at a given SNP are determined to detect the genotype at that SNP. In some embodiments, the presence of a "GG" genotype at rs2063979, a "T" allele or "CT" genotype at rs2228428, a "G" allele or "GG" genotype at rs4151117, a "T" allele or "TT" genotype at rs223895, or a "T" allele at rs16951657 indicates that the subject has an increased risk of developing PCa, and the presence of a "C" allele at rs2812377, or an "A" allele or "AA" genotype at rs2284553, indicates that the subject has a decreased risk of developing PCa. In some embodiments, the methods include determining the identity of one, two or more alleles selected from the group consisting of rs1719147, rs854680, rs2063979, rs779850, rs6770096, rs2069716, rs14304, rs779850, and rs2300295 in the subject. In some embodiments, the presence of an "AA" genotype at rs1719147, a "T" allele at rs854680, a "G" allele at rs2063979, a "TT" genotype at rs779850, a "T" allele at rs6770096, or a "G" allele at rs2069716, indicates that the subject has an increased risk of developing aggressive PCa, and the presence of a "GA" genotype at rs1719147, an "A" allele at rs14304, a "CT" genotype at rs779850, or an "A" allele at rs2300295 indicates that the subject has a decreased risk of developing aggressive PCa. In some embodiments, the methods include detecting a haplotype comprising rs11574914, rs2023305, and rs223895 to predict aggressive disease. "G" is Guanine, "A" is Adenine, "T" is Thymine, and "C" is Cytosine.

In some embodiments, where the subject has been identified using a method described herein as having an increased risk of PCa or aggressive PCa, the methods include one or more of: determining that the subject has an increased risk based on the presence of an allele or genotype described herein; diagnosing or identifying the subject as having increased risk; assigning a level of risk to the subject based on the presence of the allele or genotype; advising the subject that they have an increased risk of developing PCa or aggressive PCa, and optionally instructing the subject to perform self-monitoring of symptoms and/or self-evaluation of prostate tissues; advising the subject that their family members may also have an increased risk of developing PCa or aggressive PCa; advising the subject's family members that they may also have an increased risk of developing PCa or aggressive PCa, and optionally determining the identity of the allele or genotype associated with risk of developing PCa or aggressive PCa present in the subject in one or more family members; advising the subject to request additional monitoring or treatment for PCa; providing information to the subject regarding their increased risk of developing PCa or aggressive PCa; noting the subject's risk level and/or the identity of the allele or genotype detected in a database or medical history; informing the subject's health care provider that the subject has an increased risk; modifying a database or the subject's medical history to indicate the allele or genotype and/or risk of developing PCa or aggressive PCa; selecting the subject for a prophylactic treatment (e.g., to decrease risk); selecting the subject for increased monitoring, e.g., monitoring that is begun earlier or occurs more frequently than in subjects who do not have increased risk; monitoring the subject for development of PCa, e.g., by one or more of self-examination, self-monitoring for one or more symptoms of PCa as known in the art, examination by a health care provider, performing an imaging study to detect the development of PCa, performing one or more blood tests, e.g., to detect levels of Prostate Serum Antigen (PSA) that are associated with PCa, performing a biopsy to detect cancerous cells; selecting the subject for inclusion in a clinical trial; and/or excluding the subject from inclusion in a clinical trial. In some embodiments, the methods further include administering a treatment to the subject, e.g., a prophylactic treatment, e.g., to decrease their risk of developing PCa, or a treatment for PCa. In some embodiments, the methods include surgical removal of the prostate. In some embodiments, where the subject has PCa and has been identified as being at increased risk of developing aggressive disease by a method described herein, the methods further include administering a treatment for PCa as known in the art, e.g., surgical removal of the prostate. In some embodiments, the methods include selectively administering a treatment for PCa to a subject who has been identified as having an increased risk of developing PCa or aggressive PCa.

In some embodiments, where the subject has been identified using a method described herein as having a decreased risk of PCa or aggressive PCa, the methods include one or more of: determining that the subject has a decreased risk based on the presence of an allele or genotype described herein; diagnosing or identifying the subject as having a decreased risk; advising the subject that they have a decreased risk of developing PCa or aggressive PCa; advising the subject that they have a decreased risk of developing PCa or aggressive PCa, and optionally instructing the subject to perform self-monitoring of symptoms and/or self-evaluation of prostate tissues; advising the subject that their family members may also have a decreased risk of developing PCa or aggressive PCa; advising the subject's family members that they may also have a decreased risk of developing PCa or aggressive PCa, and optionally determining the identity of the allele or genotype associated with risk of developing PCa or aggressive PCa present in the subject in one or more family members; providing information to the subject regarding their decreased risk of developing PCa or aggressive PCa; assigning a level of risk to the subject based on the presence of the allele or genotype; noting the subject's risk level in a database or medical history; informing the subject's health care provider that the subject has an increased risk; modifying a database or the subject's medical history to indicate the allele or genotype and risk of developing PCa or aggressive PCa; selecting the subject for decreased monitoring, e.g., monitoring that is begun later or occurs less frequently than in subjects who have increased risk; selecting the subject for inclusion in a clinical trial; and/or excluding the subject from inclusion in a clinical trial. In some embodiments, where the subject has PCa and has been identified as being at decreased risk of developing aggressive disease by a method described herein, the methods further include treating the subject conservatively, e.g., by watchful waiting.

In a further aspect, the invention includes methods for determining a subject's risk for developing BrCa. The methods can include obtaining a sample comprising genomic DNA (gDNA) from the subject, and determining the identity, absence or presence of polymorphisms as described herein. In some embodiments, the methods include obtaining a test haplotype for the subject comprising polymorphisms of CCL16, CCL7, CCL23, CCL4, CCL4, CCR8, CXCL16, IFNGR1, and/or IFNGR2, wherein the haplotype provides information regarding the subject's risk of developing BrCa.

In some embodiments, the methods include determining the identity of one, two or more alleles selected from the group consisting of rs223895, rs10491121, rs1719147, rs12107527, rs2304973, rs3799488, rs2063979, rs854656, rs1719147, and rs8131980 in the subject, e.g., in a sample from the subject. In some embodiments, the presence of a "T" allele at rs223895, an "AA" genotype at rs10491121, an "AA" genotype at rs1719147, a "TT" genotype at rs12107527, a "T" allele at rs2304973, or a "C" allele at rs3799488, indicates that the subject has an increased risk of developing BrCa, and a "GG" haplotype at rs2063979, a "C" allele at rs854656, an "AG" genotype at rs1719147, or an "A" allele at rs8131980, indicates that the subject has a decreased risk of developing BrCa.

In some embodiments, where the subject has been identified using a method described herein as having an increased risk of BrCa, the methods include one or more of: determining that the subject has an increased risk based on the presence of an allele or genotype described herein; diagnosing or identifying the subject as having increased risk; assigning a level of risk to the subject based on the presence of the allele or genotype; advising the subject that they have an increased risk of developing BrCa, and optionally instructing the subject to perform self-monitoring of symptoms and/or self-evaluation of breast tissues; advising the subject that their family members may also have an increased risk of developing BrCa; advising the subject's family members that they may also have an increased risk of developing BrCa, and optionally determining the identity of the allele or genotype associated with risk of developing BrCa present in the subject in one or more family members; advising the subject to request additional monitoring or treatment for BrCa; providing information to the subject regarding their increased risk of developing BrCa; noting the subject's risk level and/or the identity of the allele or genotype detected in a database or medical history; informing the subject's health care provider that the subject has an increased risk; modifying a database or the subject's medical history to indicate the allele or genotype and/or risk of developing BrCa; selecting the subject for a prophylactic treatment (e.g., to decrease risk) of BrCa; selecting the subject for increased monitoring, e.g., monitoring that is begun earlier or occurs more frequently than in subjects who do not have increased risk; monitoring the subject for development of BrCa, e.g., by one or more of self-examination, self-monitoring for one or more symptoms of BrCa as known in the art, examination by a health care provider, performing an imaging study to detect the development of BrCa, performing one or more blood tests, e.g., to detect levels of a marker that are associated with BrCa, performing a biopsy to detect cancerous cells; selecting the subject for inclusion in a clinical trial; and/or excluding the subject from inclusion in a clinical trial. In some embodiments, the methods further include administering a treatment to the subject, e.g., a prophylactic treatment, e.g., to decrease their risk of developing BrCa, or a treatment for BrCa. In some embodiments, the methods include surgical removal of breast tissue. In some embodiments, the methods include selectively administering a treatment for BrCa to a subject who has been identified as having an increased risk of developing BrCa.

In some embodiments, where the subject has been identified using a method described herein as having a decreased risk of BrCa, the methods include one or more of: determining that the subject has a decreased risk based on the presence of an allele or genotype described herein; diagnosing or identifying the subject as having a decreased risk; advising the subject that they have a decreased risk of developing BrCa; advising the subject that they have a decreased risk of developing BrCa, and optionally instructing the subject to perform self-monitoring of symptoms and/or self-evaluation of prostate tissues; advising the subject that their family members may also have a decreased risk of developing BrCa; advising the subject's family members that they may also have a decreased risk of developing BrCa, and optionally determining the identity of the allele or genotype associated with risk of developing BrCa present in the subject in one or more family members; providing information to the subject regarding their decreased risk of developing BrCa; assigning a level of risk to the subject based on the presence of the allele or genotype; noting the subject's risk level in a database or medical history; informing the subject's health care provider that the subject has an increased risk; modifying a database or the subject's medical history to indicate the allele or genotype and risk of developing BrCa; selecting the subject for decreased monitoring, e.g., monitoring that is begun later or occurs less frequently than in subjects who have increased risk; selecting the subject for inclusion in a clinical trial; and/or excluding the subject from inclusion in a clinical trial.

Information obtained using a method described herein can be used, e.g., to select a subject population for a clinical trial, to stratify a subject population in a clinical trial, and/or to stratify subjects that respond to a treatment from those who do not respond to a treatment, or subjects that have negative side effects from those who do not.

In another aspect, the invention provides methods for selecting a subject for inclusion in or exclusion from a clinical trial, e.g., a trial of a treatment for PCa or BrCa. The methods include obtaining a haplotype for the subject including one, two or more of the polymorphisms described herein; determining whether the genetic profile is associated with an increased risk of developing PCa or BrCa; and including or excluding the subject in the trial based on the genetic profile, e.g., if the genetic profile indicates that the subject has (or does not have) an increased risk of developing PCa or BrCa.

In another aspect, the invention provides methods for selecting a subject for administration of a treatment for PCa. The methods include obtaining a genetic profile for the subject, wherein the genetic profile comprises one, two or more of the polymorphisms described herein; determining whether the genetic profile is associated with an increased risk of developing PCa, e.g., aggressive PCa, or BrCa; and administering the treatment to the subject if the genetic profile indicates that the subject has an increased risk of developing PCa, e.g., aggressive PCa, or BrCa.

In another aspect, the invention provides methods for selecting a treatment for administration to a subject. The methods include obtaining a genetic profile for the subject, wherein the genetic profile includes one, two or more of the polymorphisms described herein; determining whether the genetic profile is associated with an increased risk of developing PCa or BrCa; and administering the treatment for PCa or BrCa to the subject if the genetic profile indicates that the subject has an increased risk of developing PCa or BrCa.

In some embodiments of the methods described herein, the subject is of European descent.

In some embodiments, the methods described herein include determining the identity of alleles at CCL16_rs2063979, CCR4_rs2228428, CX3CL1_rs4151117, CCL17_rs223895, PIAS1_rs16951657, CCL21_rs2812377, IFNGR2_rs2284553, CCL18_rs14304 or XCL1_rs2300295. The presence of one or more minor allele at CCL16_rs2063979, CCR4_rs2228428, CX3CL1_rs4151117, CCL17_rs223895, or PIAS1_rs16951657 is associated with an 1.25 to 1.56-fold increase in the risk of developing PCA ($p \leq 0.049$). In contrast, possession at least one minor CCL21_rs2812377C allele or the IFNGR2_rs2284553AA genotype was linked to a marginal 16 to 23% decrease in risk ($p \leq 0.041$). With respect to disease aggressiveness, the presence of two CCL18_rs14304 or XCL1_rs2300295 minor alleles is related to a 36-40% reduction in aggressive PCA ($p \leq 0.045$), relative to those with the referent genotype.

As used herein, the terms "increased" or "decreased" risk is determined relative to subjects lacking the specified genotype, e.g., with the referent genotype (as shown in Tables 1-4).

Also provided herein are kits for use in detection of genetic profiles associated with PCa, including at least one nucleic acid probe that hybridizes to a sequence that includes a polymorphism described herein, or can be used to amplify a sequence that includes a polymorphism described herein. In some embodiments, determining the identity of an allele comprises contacting the sample with a probe specific for a selected allele, and detecting the formation of complexes between the probe and the selected allele, wherein the formation of complexes between the probe and the selected allele indicates the presence of the selected allele in the sample.

Also provided are arrays that include a substrate having a plurality of addressable areas, wherein one or more of the addressable areas includes one or more probes that can be used to detect a polymorphism described herein.

As used herein, a "genetic profile" is one or a set of signature genetic changes (e.g., polymorphisms). A "genetic profile" as used herein is information regarding the presence or absence of one or more genetic markers (i.e., alleles described herein) in a subject. A genetic profile can consist of a variety of genetic markers, including indels (insertions or deletions of the DNA at particular locations on the chromosome); single nucleotide polymorphisms (SNPs) in which a particular nucleotide is changed; microsatellites; and minisatellites. A "haplotype" is one or a set of signature genetic changes (i.e., a genetic profile) that includes markers that are normally grouped closely together on the DNA strand, and are usually inherited as a group;

"Linkage disequilibrium" refers to when the observed frequencies of haplotypes in a population does not agree with haplotype frequencies predicted by multiplying together the frequency of individual genetic markers in each haplotype.

The term "chromosome" as used herein refers to a gene carrier of a cell that is derived from chromatin and comprises DNA and protein components (e.g., histones). The conventional and internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs. For example, the size of the entire human genome is about $3 \times 10^9$ base pairs.

The term "gene" refers to a DNA sequence in a chromosome that encodes a gene product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used. Targets for hybridization can be derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intra-specific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., *Current Protocols in Molecular Biology*, John Wiley & Sons, N.Y. (2003), 6.3.1-6.3.6. Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30%, e.g., at least 40%, 50%, 60%, 70%, 80%, 90% or 100%, of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80%, e.g., 85%, 90%, 95%, 97% or more, identical.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

As used herein, the term "stratification" refers to the creation of a distinction between subjects on the basis of a characteristic or characteristics of the subjects. Generally, in the context of clinical trials, the distinction is used to distinguish responses or effects in different sets of patients distinguished according to the stratification parameters. In some embodiments, stratification includes distinction of subject groups based on the presence or absence of particular markers or genetic profiles described herein. The stratification can be performed, e.g., in the course of analysis, or can be used in creation of distinct groups or in other ways.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 is a list of the sequences associated with the SNPs described herein. The sequences show the 30 nucleotides flanking the SNPs on the 3' and 5' sides, and the major and minor alleles at each SNP.

DETAILED DESCRIPTION

Interactions among highly variant genes, central to angiogenesis, may modulate susceptibility for breast and prostate cancer, as previous demonstrated. The expression of several cancer metastasis-promoting genes (autocrine mobility factor receptor, chemokine receptor (CCXR) 4, chemokine ligand (CCL) 5, chemokine receptor (CCR) 7 and matrix metalloproteinase (MMP) 9) were validated via qRT-PCR and shown to have significantly higher levels in tumors from African-Americans than European-Americans. These receptors may serve as interesting targets to design drugs that fight prostate tumor metastasis.

The present inventors have identified new targets and validated individual and joint modifying effects of chemokine-associated single nucleotide polymorphisms (SNPs) in relation to PCa or BrCa risk and disease prognosis using a case-control study design.

As described herein, the inheritance of the CCL16_rs2063979 "GG" (under the recessive genetic model), CCR4_rs2228428 "CT" or "CT+TT", CX3CL1_rs4151117 "GG", CCL17_rs223895 "TT", or PIAS1_rs16951657 "GT" or "GT+TT" was associated with an 1.25 to 1.56-fold increase in the risk of developing PCA ($p \leq 0.049$). In contrast, possession at least one minor CCL21_rs2812377 "C" allele or the IFNGR2_rs2284553 "AA" genotype was linked to a marginal 16 to 23% decrease in risk ($p \leq 0.041$). With respect to disease aggressiveness, inheritance the CCL4 rs1719147 "GA", CCL18_rs14304 "GA" or XCL1_rs2300295 "AA" genotypes were related to a 36-40% reduction in aggressive PCA ($p \leq 0.045$), relative to those with the referent genotype. In contrast, inheritance of the CCL16 rs854680 "TT", CCL16 rs2063979 "AG+GG", CCL28 rs779850 "TT", CCR4 rs6770096 "CT", IFNG rs2069716 "AG+GG" genotypes were linked to a 1.41-2.50 fold increase in the risk of developing aggressive prostate cancer.

In addition, possession of the CCL16_rs2063979 "GG" (under the recessive genetic model), CCL23 rs854656 "GG" (under the recessive genetic model), or IFNGR2 rs8131980 "GA+AA" genotypes was linked with a 21-37% reduction in BrCa risk after adjusting for age. Inheritance of the CCL17 rs223895 "CT+TT", CCR8 rs12107527 "TT" (under the recessive genetic model), or the CXCL16 rs2304973 "TT" (under the recessive genetic model) genotypes were associated with a 20-39% increase in the risk of developing BrCa.

Methods of Diagnoses and Evaluation of Risk

Described herein are a variety of methods for the diagnosis of susceptibility to PCa or BrCa. "Susceptibility" does not necessarily mean that the subject will develop PCa or BrCa, but rather that the subject is, in a statistical sense, more likely to develop PCa or BrCa than a member of the general population, i.e., has an increased risk of developing PCa or BrCa. As used herein, susceptibility to PCa or BrCa exists if the subject has a genetic profile associated with an increased risk of PCa or BrCa as described herein. Ascertaining whether the subject has such a genetic profile is included in the concept of diagnosing susceptibility to PCa or BrCa as used herein. Such determination is useful, for example, for purposes of diagnosis, treatment selection, and genetic counseling. Thus, the methods described herein can include obtaining a genetic profile associated with an increased risk of PCa or BrCa as described herein for the subject.

As used herein, "obtaining a genetic profile" includes obtaining information regarding the identity, presence or absence of one or more genetic markers in a subject. Obtaining a genetic profile can, but need not, include obtaining a sample comprising DNA from a subject, and/or assessing the identity, presence or absence of one or more genetic markers in the sample. The individual or organization who obtains the genetic profile need not actually carry out the physical analysis of a sample from a subject; the genetic profile can include information obtained by analysis of the sample by a third party. Thus the methods can include steps that occur at more than one site. For example, a sample can be obtained from a subject at a first site, such as at a health care provider, or at the subject's home in the case of a self-testing kit. The sample can be analyzed at the same or a second site, e.g., at a laboratory or other testing facility.

Obtaining a genetic profile can also include or consist of reviewing a subject's medical history, where the medical history includes information regarding the identity, presence or absence of one or more genetic markers in the subject, e.g., results of a genetic test.

In some embodiments, to detect the presence of a genetic profile described herein, a biological sample that includes nucleated cells (such as blood, a cheek swab or mouthwash) is prepared and analyzed for the presence or absence of preselected markers. Such diagnoses may be performed by diagnostic laboratories, or, alternatively, diagnostic kits can be manufactured and sold to health care providers or to private individuals for self-diagnosis. Diagnostic or prognostic tests can be performed as described herein or using well known techniques, such as described in U.S. Pat. No. 5,800,998.

Results of these tests, and optionally interpretive information, can be returned to the subject, the health care provider or to a third party payor. The results can be used in a number of ways. The information can be, e.g., communicated to the tested subject, e.g., with a prognosis and optionally interpretive materials that help the subject understand the test results and prognosis. The information can be used, e.g., by a health care provider, to determine whether to administer a specific drug, or whether a subject should be assigned to a specific category, e.g., a category associated with a specific disease endophenotype, or with drug response or non-response. The information can be used, e.g., by a third party payor such as a healthcare payer (e.g., insurance company or HMO) or other agency, to determine whether or not to reimburse a health care provider for services to the subject, or whether to approve the provision of services to the subject. For example, the healthcare payer may decide to reimburse a health care provider for treatments for PCa or BrCa if the subject has an increased risk of developing PCa or BrCa. As another example, a drug or treatment may be indicated for individuals with a certain genetic profile, and the insurance company would only reimburse the health care provider (or the insured individual) for prescription or purchase of the drug if the insured individual has that genetic profile. The presence or absence of the genetic profile in a patient may be ascertained by using any of the methods described herein.

Information gleaned from the methods described herein can also be used to select or stratify subjects for a clinical trial. For example, the presence of a selected genetic profile described herein can be used to select a subject for a trial. The information can optionally be correlated with clinical information about the subject, e.g., diagnostic or endophenotypic information.

Genetic Profiles Associated with PCa or BrCa

As described herein, genetic profiles associated with PCa include those SNPs listed in Table 1; genetic profiles associated with aggressive PCa include those SNPs listed in Table 2; and genetic profiles associated with BrCa include those SNPs listed in Tables 3 (and haplotypes listed in table 4).

Linkage Disequilibrium Analysis

Linkage disequilibrium (LD) is a measure of the degree of association between alleles in a population. One of skill in the art will appreciate that genetic profiles involving markers within 1 Linkage Disequilibrium Unit (LDU) of the polymorphisms described herein can also be used in a similar manner to those described herein. LDUs share an inverse relationship with LD so that regions with high LD (such as haplotype blocks) have few LDUs and low recombination, whilst regions with many LDUs have low LD and high recombination. Methods of calculating LDUs are known in the art (see, e.g., Morton et al., Proc Natl Acad Sci USA 98(9):5217-21 (2001); Tapper et al., Proc Natl Acad Sci USA 102(33):11835-11839 (2005); Maniatis et al., Proc Natl Acad Sci USA 99:2228-2233 (2002)).

Thus, in some embodiments, the methods include analysis of polymorphisms that are within 1 LDU of a polymorphism described herein. Methods are known in the art for identifying such polymorphisms; for example, the International HapMap Project provides a public database that can be used, see hapmap.org, as well as The International HapMap Consortium, Nature 426:789-796 (2003), and The International HapMap Consortium, Nature 437:1299-1320 (2005). Generally, it will be desirable to use a HapMap constructed using data from individuals who share ethnicity with the subject, e.g., a HapMap for African-Americans would ideally be used to identify markers within 1 LDU of a marker described herein for use in genotyping a subject of African American descent.

Alternatively, methods described herein can include analysis of polymorphisms that are within a value defined by Lewontin's D' (linkage disequilibrium parameter, see Lewontin, Genetics 49:49-67 (1964)) of a polymorphism described herein. Results can be obtained, e.g., from on line public resources such as HapMap.org. The simple linkage disequilibrium parameter (D) reflects the degree to which alleles at two loci (for example two SNPs) occur together more often (positive values) or less often (negative values) than expected in a population as determined by the products of their respective allele frequencies. For any two loci, D can vary in value from −0.25 to +0.25. However, the magnitude of D (Dmax) varies as function of allele frequencies. To control for this, Lewontin introduced the D' parameter, which is D/Dmax and varies in value from −1 (alleles never observed together) to +1 (alleles always observed together). Typically, the absolute value of D' (i.e., |D'|) is reported in online databases, because it follows mathematically that positive association for one set of alleles at two loci corresponds to a negative association of equal magnitude for the reciprocal set. This disequilibrium parameter varies from 0 (no association of alleles at the two loci) to 1 (maximal possible association of alleles at the two loci).

Thus, in some embodiments, the methods include analysis of polymorphisms that are within D'>0.75, or D'=1, for pairwise comparisons, of a polymorphism described herein.

Methods of Determining the Presence or Absence of a Genetic Profile Associated with Risk of Developing PCa or BrCa The methods described herein include determining the presence or absence of genetic profiles associated with PCa or BrCa. In some embodiments, an association with PCa or BrCa is determined by the presence of a shared genetic profile between the subject and an affected reference individual, e.g., a first or second-degree relation of the subject, and the absence of the genetic profile in an unaffected reference individual. Thus the methods can include obtaining and analyzing a sample from a suitable reference individual.

Samples that are suitable for use in the methods described herein contain genetic material, e.g., genomic DNA (gDNA). Non-limiting examples of sources of samples include urine, blood, and tissue. The sample itself will typically consist of nucleated cells (e.g., blood or buccal cells), tissue, etc., removed from the subject. The subject can be an adult, child, fetus, or embryo. In some embodiments, the sample is obtained prenatally, either from a fetus or embryo or from the mother (e.g., from fetal or embryonic cells in the maternal circulation). Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

The sample may be further processed before the detecting step. For example, DNA in a cell or tissue sample can be separated from other components of the sample. The sample can be concentrated and/or purified to isolate DNA. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., 2003, supra. All samples obtained from a subject, including those subjected to any sort of further processing, are considered to be obtained from the subject.

The absence or presence of a genetic profile associated with PCa or BrCa as described herein can be determined using methods known in the art, e.g., gel electrophoresis, capillary electrophoresis, size exclusion chromatography, sequencing, and/or arrays to detect the presence or absence of the marker(s) of the genetic profile. Amplification of nucleic acids, where desirable, can be accomplished using methods known in the art, e.g., PCR.

Methods of nucleic acid analysis to detect polymorphisms and/or polymorphic variants include, e.g., microarray analysis. Hybridization methods, such as Southern analysis, Northern analysis, or in situ hybridizations, can also be used (see *Current Protocols in Molecular Biology*, Ausubel, F. et al., eds., John Wiley & Sons 2003). To detect microdeletions, fluorescence in situ hybridization (FISH) using DNA probes that are directed to a putatively deleted region in a chromosome can be used. For example, probes that detect all or a part of a microsatellite marker can be used to detect microdeletions in the region that contains that marker.

Other methods include direct manual sequencing (Church and Gilbert, Proc. Natl. Acad. Sci. USA 81:1991-1995 (1988); Sanger et al., Proc. Natl. Acad. Sci. 74:5463-5467 (1977); Beavis et al. U.S. Pat. No. 5,288,644); automated fluorescent sequencing; single-stranded conformation polymorphism assays (SSCP); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., Proc. Natl. Acad. Sci. USA 86:232-236 (1989)), mobility shift analysis (Orita et al., Proc. Natl. Acad. Sci. USA 86:2766-2770 (1989)), restriction enzyme analysis (Flavell et al., Cell 15:25 (1978); Geever et al., Proc. Natl. Acad. Sci. USA 78:5081 (1981)); quantitative real-time PCR (Raca et al., Genet Test 8(4):387-94 (2004)); heteroduplex analysis; chemical mismatch cleavage (CMC) (Cotton et al., Proc. Natl. Acad. Sci. USA 85:4397-4401 (1985)); RNase protection assays (Myers et al., Science 230:1242 (1985)); use of polypeptides that recognize nucleotide mismatches, e.g., *E. coli* mutS protein; allele-specific PCR, for example. See, e.g., U.S. Patent Publication No. 2004/0014095, to Gerber et al., which is incorporated herein by reference in its entirety. In some embodiments, the sequence is determined on both strands of DNA.

In order to detect polymorphisms and/or polymorphic variants, it will frequently be desirable to amplify a portion of genomic DNA (gDNA) encompassing the polymorphic site. Such regions can be amplified and isolated by PCR using oligonucleotide primers designed based on genomic and/or cDNA sequences that flank the site. See e.g., *PCR Primer: A Laboratory Manual*, Dieffenbach and Dveksler, (Eds.); McPherson et al., *PCR Basics: From Background to Bench* (Springer Verlag, 2000); Mattila et al., Nucleic Acids Res., 19:4967 (1991); Eckert et al., *PCR Methods and Applications*, 1:17 (1991); *PCR* (eds. McPherson et al., IRL Press, Oxford); and U.S. Pat. No. 4,683,202. Other amplification methods that may be employed include the ligase chain reaction (LCR) (Wu and Wallace, Genomics, 4:560 (1989), Landegren et al., Science, 241:1077 (1988), transcription amplification (Kwoh et al., Proc. Natl. Acad. Sci. USA, 86:1173 (1989)), self-sustained sequence replication (Guatelli et al., Proc. Nat. Acad. Sci. USA, 87:1874 (1990)), and nucleic acid based sequence amplification (NASBA). Guidelines for selecting primers for PCR amplification are well known in the art. See, e.g., McPherson et al., *PCR Basics: From Background to Bench*, Springer-Verlag, 2000. A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

In one example, a sample (e.g., a sample comprising genomic DNA), is obtained from a subject. The DNA in the sample is then examined to determine a genetic profile as described herein. The genetic profile can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)-glycine units, with an organic base (A, G, C, T or U) attached to the glycine nitrogen via a methylene carbonyl linker (see, e.g., Nielsen et al., *Bioconjugate Chemistry*, The American Chemical Society, 5:1 (1994)). The PNA probe can be designed to specifically hybridize to a nucleic acid comprising a polymorphic variant conferring susceptibility to or indicative of the presence of PCa or BrCa.

In some embodiments, restriction digest analysis can be used to detect the existence of a polymorphic variant of a polymorphism, if alternate polymorphic variants of the polymorphism result in the creation or elimination of a restriction site. A sample containing genomic DNA is obtained from the individual. Polymerase chain reaction (PCR) can be used to amplify a region comprising the polymorphic site, and restriction fragment length polymorphism analysis is conducted (see Ausubel et al., *Current Protocols in Molecular Biology*, supra). The digestion pattern of the relevant DNA fragment indicates the presence or absence of a particular polymorphic variant of the polymorphism and is therefore indicative of the presence or absence of susceptibility to PCa or BrCa.

Sequence analysis can also be used to detect specific polymorphic variants. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined.

Allele-specific oligonucleotides can also be used to detect the presence of a polymorphic variant, e.g., through the use of dot-blot hybridization of amplified oligonucleotides with allele-specific oligonucleotide (ASO) probes (see, for example, Saiki et al., Nature (London) 324:163-166 (1986)). An "allele-specific oligonucleotide" (also referred to herein as an "allele-specific oligonucleotide probe") is typically an oligonucleotide of approximately 10-50 base pairs, preferably approximately 15-30 base pairs, that specifically hybridizes to a nucleic acid region that contains a polymorphism. An allele-specific oligonucleotide probe that is specific for particular a polymorphism can be prepared using standard methods (see Ausubel et al., *Current Protocols in Molecular Biology*, supra).

Generally, to determine which of multiple polymorphic variants is present in a subject, a sample comprising DNA is obtained from the individual. PCR can be used to amplify a portion encompassing the polymorphic site. DNA containing the amplified portion may be dot-blotted, using standard methods (see Ausubel et al., *Current Protocols in Molecular Biology*, supra), and the blot contacted with the oligonucleotide probe. The presence of specific hybridization of the probe to the DNA is then detected. Specific hybridization of an allele-specific oligonucleotide probe (specific for a polymorphic variant indicative of susceptibility to PCa or BrCa) to DNA from the subject is indicative of susceptibility to PCa or BrCa.

In some embodiments, fluorescence polarization template-directed dye-terminator incorporation (FP-TDI) is used to determine which of multiple polymorphic variants of a polymorphism is present in a subject (Chen et al., (1999) Genome Research, 9(5):492-498). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

Real-time pyrophosphate DNA sequencing is yet another approach to detection of polymorphisms and polymorphic variants (Alderborn et al., (2000) Genome Research, 10(8): 1249-1258). Additional methods include, for example, PCR amplification in combination with denaturing high performance liquid chromatography (dHPLC) (Underhill, P. A., et al., Genome Research, Vol. 7, No. 10, pp. 996-1005, 1997).

The methods can include determining the genotype of a subject with respect to both copies of the polymorphic site present in the genome. For example, the complete genotype may be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to certain embodiments of the invention.

Probes

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70%, e.g., 80%, 90%, 95%, 98% or more identity to the target sequence. The probe sequence must also be sufficiently long so that the probe exhibits selectivity for the target sequence over non-target sequences. For example, the probe will be at least 20, e.g., 25, 30, 35, 50, 100, 200, 300, 400, 500, 600, 700, 800, 900 or more, nucleotides in length. In some embodiments, the probes are not more than 30, 50, 100, 200, 300, 500, 750, or 1000 nucleotides in length. Probes are typically about 20 to about $1 \times 10^6$ nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

In some embodiments, the probe is a test probe, e.g., a probe that can be used to detect polymorphisms in a region described herein, e.g., polymorphisms as described herein.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially, e.g., from Applied Biosystems, e.g., the Assays-on-Demand SNP kits Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic. Histochem., 1998, 73(1):6-22, Wheeless et al., Cytometry 1994, 17:319-326, and U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4, 4-difluoro-5,7-dimethyl-4-bora-3a,4a diaza-3-indacenepropionic acid, eosin-5-isothiocyanate, erythrosin-5-isothiocyanate, and Cascade™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^3H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end) will generally hybridize preferentially to a nucleic acid comprising that sequence, as opposed to a nucleic acid comprising an alternate polymorphic variant.

Arrays and Uses Thereof

In another aspect, the invention features arrays that include a substrate having a plurality of addressable areas, and methods of using them. At least one area of the plurality includes a nucleic acid probe that binds specifically to a sequence comprising a polymorphism described herein, and can be used to detect the absence or presence of said polymorphism, e.g., one or more SNPs, microsatellites, minisatellites, or indels, as described herein, to determine a genetic profile. For example, the array can include one or more nucleic acid probes that can be used to detect a polymorphism listed in Tables 1-3. In some embodiments, the array further includes at least one area that includes a nucleic acid probe that can be used to specifically detect another marker associated with PCa or BrCa, as described herein. The substrate can be, e.g., a two-dimensional substrate known in the art such as a glass slide, a wafer (e.g., silica or plastic), a mass spectroscopy plate, or a three-dimensional substrate such as a gel pad. In some embodiments, the probes are nucleic acid capture probes.

Methods for generating arrays are known in the art and include, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145). The array typically includes oligonucleotide probes capable of specifically hybridizing to different polymorphic variants. According to the method, a nucleic acid of interest, e.g., a nucleic acid encompassing a polymorphic site, (which is typically amplified) is hybridized with the array and scanned. Hybridization and scanning are generally carried out according to standard methods. See, e.g., Published PCT Application Nos. WO 92/10092 and WO 95/11995, and U.S. Pat. No. 5,424,186. After hybridization and washing, the array is scanned to determine the position on the array to which the nucleic acid hybridizes. The hybridization data obtained from the scan is typically in the form of fluorescence intensities as a function of location on the array.

Arrays can include multiple detection blocks (i.e., multiple groups of probes designed for detection of particular polymorphisms). Such arrays can be used to analyze multiple different polymorphisms. Detection blocks may be grouped within a single array or in multiple, separate arrays so that varying conditions (e.g., conditions optimized for particular polymorphisms) may be used during the hybridization. For example, it may be desirable to provide for the detection of those polymorphisms that fall within G-C rich stretches of a genomic sequence, separately from those falling in A-T rich segments.

Additional description of use of oligonucleotide arrays for detection of polymorphisms can be found, for example, in U.S. Pat. Nos. 5,858,659 and 5,837,832. In addition to oligonucleotide arrays, cDNA arrays may be used similarly in certain embodiments of the invention.

The methods described herein can include providing an array as described herein; contacting the array with a sample, e.g., a portion of genomic DNA that includes at least a portion of human chromosome 4p and/or 22q, e.g., a region between SNP rs801720 and SNP rs710123, e.g., a region between SNP rs713692 and rs756638, optionally, a different portion of genomic DNA, e.g., a portion that includes a different portion of human chromosomes 22 and/or 4, or another chromosome, e.g., including another region associated with PCa or BrCa., and detecting binding of a nucleic acid from the sample to the array. Optionally, the method includes amplifying nucleic acid from the sample, e.g., genomic DNA that includes a portion of a human chromosome described herein, and, optionally, a region that includes another region associated with PCa or BrCa, prior to or during contact with the array.

In some aspects, the methods described herein can include using an array that can ascertain differential expression patterns or copy numbers of one or more genes in samples from normal and affected individuals (see, e.g., Redon et al., Nature. 444(7118):444-54 (2006)). For example, arrays of probes to a marker described herein can be used to measure polymorphisms between DNA from a subject having PCa or BrCa, and control DNA, e.g., DNA obtained from an individual that does not have PCa or BrCa, and has no risk factors for PCa or BrCa. Since the clones on the array contain sequence tags, their positions on the array are accurately known relative to the genomic sequence. Different hybridization patterns between DNA from an individual afflicted with PCa or BrCa and DNA from a normal individual at areas in the array corresponding to markers in human chromosome 4p and/or 22q as described herein, and, optionally, one or more other regions associated with PCa or BrCa, are indicative of a risk of PCa or BrCa. Methods for array production, hybridization, and analysis are described, e.g., in Snijders et al., (2001) Nat. Genetics 29:263-264; Klein et al., (1999) Proc. Natl. Acad. Sci. U.S.A. 96:4494-4499; Albertson et al., (2003) Breast Cancer Research and Treatment 78:289-298; and Snijders et al. "BAC microarray based comparative genomic hybridization." In: Zhao et al. (eds), *Bacterial Artificial Chromosomes: Methods and Protocols*, Methods in Molecular Biology, Humana Press, 2002. Real time quantitative PCR can also be used to determine copy number.

In another aspect, the invention features methods of determining the absence or presence of a genetic profile associated with PCa or BrCa as described herein, using an array described above. The methods include providing a two dimensional array having a plurality of addresses, each address of the plurality being positionally distinguishable from each other address of the plurality having a unique nucleic acid capture probe, contacting the array with a first sample from a test subject who is suspected of having or being at risk for PCa or BrCa, and comparing the binding of the first sample with one or more references, e.g., binding of a sample from a subject who is known to have PCa or BrCa, and/or binding of a sample from a subject who is unaffected, e.g., a control sample from a subject who neither has, nor has any risk factors for PCa or BrCa. In some embodiments, the methods include contacting the array with a second sample from a subject who has PCa or BrCa; and comparing the binding of the first sample with the binding of the second sample. In some embodiments, the methods include contacting the array with a third sample from a cell or subject that does not have PCa or BrCa and is not at risk for PCa or BrCa; and comparing the binding of the first sample with the binding of the third sample. In some embodiments, the second and third samples are from first or second-degree relatives of the test subject. Binding, e.g., in the case of a nucleic acid hybridization, with a capture probe at an address of the plurality, can be detected by any method known in the art, e.g., by detection of a signal generated from a label attached to the nucleic acid.

Prostate Cancer (PCa)

PCa is an uncontrolled (malignant) growth of cells in the prostate gland which is located at the base of the urinary bladder and is responsible for helping control urination as well as forming part of the semen. Prostate cancer is the second leading cause of death of males in the U.S. The methods described herein can be used to determine an individual's risk of developing PCa.

A number of risk factors for PCa are known in the art, including age (increased over 40, more increased over 50, highest over 65); race/ethnicity (highest in men of African descent, e.g., African American men, lower in Asian and Latino/Hispanic men); nationality (highest in North America, northwestern Europe, Australia, and Caribbean, lower in Asia, Africa, Central America, and South America); family history; diet (consumption of a lot od red meat and/or high-fat dairy products increases risk); obesity (BMI>29); lack of exercise; inflammation of the prostate; infection (e.g., sexually transmitted diseases); vasectomy; and other genes (e.g., HPCa1, HPCaX, BrCA1, BRCA2, CAPB, PCaP, ELAC2/HPCa2) or genetic variants associated with increased risk of PCa (1-8).

In particular, the methods described herein are useful for determining risk of developing PCa in men of African descent, e.g., West African descent. In the US alone, nearly 31,000 cases of prostate cancer were diagnosed in African American men in 2007, which accounted for 37% of all cancers diagnosed in African American men. Despite recent improvement in treatments, PCa incidence and mortality remain higher among African American men that their white counterparts. See Odedina et al., Infect. Agents Can. 4(Suppl 1):S2 (pp. 1-8) (2009).

Current Treatment of PCa

Four treatment options are presently the standard of care: Watchful waiting (closely monitoring the subject's condition without giving any treatment until symptoms appear or change, usually used in older men with other medical problems and early-stage disease); surgery (radical prostatectomy, lymphadenectomy, transurethral resection of the prostate (TURP); orchidectomy); radiation therapy (external or internal); and hormone therapy (e.g., with LHRH agonists, antiandrogens, and estrogens). In addition, a number of experimental treatments are being evaluated in clinical trials, such as cryosurgery, chemotherapy, high-intensity focused ultrasound, and biologic therapy (e.g., using PCa-specific antibodies).

Breast Cancer (BrCa)

Breast cancer (BrCa) is the second most common cancer in women, and is found in one in eight women in the United States. African-American women are more likely than all other women to die from breast cancer. Twice as many African-American women who have breast cancer die from the disease when compared to white women, although fewer African-American women get the disease. At least part of this seems to be because African-American women tend to have more aggressive tumors, although why this is the case is not known. Asian, Hispanic, and Native-American women have a lower risk of developing and dying from breast cancer. Asian women have some of the lowest breast cancer rates of any group in the world; however, the rates of breast cancer among Asians are approaching those of white women. Unlike the West where women typically present after age 50 with early stage disease, breast cancer in Asian women occurs at a younger age and is usually presented and diagnosed at a later stage of development. More patients present with locally-advanced Stage III disease in Asian countries than in the West. Further, while breast cancer mortality is declining in Europe and the U.S., in some areas, notably China, it is rising.

Methods of Determining Treatment Regimens and Methods of Treating PCa or BrCa

As described herein, the presence of certain genetic profiles described herein has been correlated with an increased risk of developing or having PCa or BrCa, or of having aggressive PCa. Thus, the new methods can also include selecting a treatment regimen for a subject determined to be at risk for developing PCa or BrCa, based upon the absence or presence of a genetic profile associated with PCa or BrCa as described herein. The determination of a treatment regimen can also be based upon the absence or presence of other risk factors associated with PCa or BrCa, e.g., as described herein. Therefore, the methods of the invention can include selecting a treatment regimen for a subject having one or more risk factors for PCa or BrCa, and having a genetic profile described herein. The methods can also include administering a treatment regimen to a subject having, or at risk for developing, PCa or BrCa to thereby treat, prevent or delay further progression of the disease.

As used herein, the term "treat" or "treatment" is defined as the application or administration of a treatment regimen, e.g., a therapeutic agent or modality, to a subject, e.g., a patient. The subject can be a patient having PCa or BrCa, a symptom of PCa or BrCa or at risk of developing (i.e., having one or more of the risk factors for PCa or BrCa known in the art or described herein) PCa or BrCa. The treatment can be to cure, heal, alleviate, relieve, alter, remedy, ameliorate, palliate, improve or affect PCa or BrCa, the symptoms of PCa or BrCa or the predisposition toward PCa or BrCa.

The methods of the invention, e.g., methods of determining a treatment regimen and methods of treatment or prevention of PCa or BrCa, can further include the step of monitoring the subject, e.g., for a change (e.g., an increase or decrease) in one or more of the diagnostic criteria for PCa or BrCa listed herein, or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same or a different therapeutic agent or modality. Generally, a decrease in one or more of the parameters described above is indicative of the improved condition of the subject, although with red blood cell and platelet levels, an increase can be associated with the improved condition of the subject.

The methods can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response genotype. In a preferred embodiment, a treatment for PCa or BrCa can be evaluated by administering the same treatment or combinations or treatments to a subject having PCa or BrCa and a genetic profile as described herein and to a subject that has PCa or BrCa but does not have a genetic profile as described herein. The effects of the treatment or combination of treatments on each of these subjects can be used to determine if a treatment or combination of treatments is particularly effective on a sub-group of subjects having PCa or BrCa. In other embodiments, various treatments or combinations of treatments can be evaluated by administering two different treatments or combinations of treatments to at least two different subjects having PCa or BrCa and a genetic profile as described herein. Such methods can be used to determine if a particular treatment or combination of treatments is more effective than others in treating this subset of PCa or BrCa patients.

Various treatment regimens are known in the art for treating PCa or BrCa.

Pharmacogenomics

With regards to both prophylactic and therapeutic methods of treatment of PCa or BrCa, such treatments may be specifically tailored or modified, based on knowledge obtained from the field of pharmacogenomics. "Pharmacogenomics," as used herein, refers to the application of genomics technologies such as structural chromosomal analysis, to drugs in clinical development and on the market, as detailed previously (e.g., Eichelbaum et al., Clin. Exp. Pharmacol. Physiol. 23:983-985 (1996) and Linder et al., Clin. Chem. 43:254-266 (1997). Specifically, as used herein, the term refers to the study of how a patient's genes determine his or her response to a drug (e.g., a patient's "drug response phenotype," or "drug response genotype"). Thus, another aspect of the invention provides methods for tailoring an individual's prophylactic or therapeutic treatment according to that individual's drug response genotype.

Information generated from pharmacogenomic research using a method described herein can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when administering a therapeutic composition, e.g., a cytotoxic agent or combination of cytotoxic agents, to a patient, as a means of treating or preventing PCa or BrCa.

In one embodiment, a physician or clinician may consider applying knowledge obtained in relevant pharmacogenomics studies, e.g., using a method described herein, when determining whether to administer a pharmaceutical composition, e.g., an anticancer agent or a combination of anticancer agents, to a subject. In another embodiment, a physician or clinician may consider applying such knowledge when determining the dosage, e.g., amount per treatment or frequency of treatments, of a treatment, e.g., an anticancer agent or combination of anticancer agents, administered to a patient.

As one example, a physician or clinician may determine (or have determined, e.g., by a laboratory) the genetic profile of a subject as described herein, and optionally one or more other markers associated with PCa or BrCa, of one or a group of subjects who may be participating in a prostate cancer clinical trial designed to test the efficacy of a pharmaceutical composition, e.g., an anticancer agent or combination of anticancer agents, and wherein the physician or clinician attempts to correlate the genotypes of the subjects with their response to the pharmaceutical composition.

As another example, information regarding a genetic profile associated with an increased risk of PCa or BrCa, as described herein, can be used to stratify or select a subject population for a clinical trial. The information can, in some embodiments, be used to stratify individuals that may exhibit a toxic response to a treatment from those that will not. In other cases, the information can be used to separate those that will be non-responders from those who will be responders. The genetic profiles described herein can be used in pharmacogenomics-based design and manage the conduct of a clinical trial, e.g., as described in U.S. Pat. Pub. No. 2003/0108938.

As another example, information regarding a genetic profile associated with an increased risk of PCa or BrCa, as described herein, can be used to stratify or select human cells or cell lines for drug testing purposes. Human cells are useful for studying the effect of a polymorphism on physiological function, and for identifying and/or evaluating potential therapeutic agents for the treatment of PCa or BrCa, e.g., chemotherapeutic agents. Thus the methods can include performing the present methods on genetic material from a cell line.

Theranostics

Also included herein are compositions and methods for the identification and treatment of subjects who have an increased risk of PCa or BrCa, such that a theranostic approach can be taken to test such individuals to determine the effectiveness of a particular therapeutic intervention (e.g., a pharmaceutical or non-pharmaceutical intervention as described herein) and to alter the intervention to 1) reduce the risk of developing adverse outcomes and 2) enhance the effectiveness of the intervention. Thus, in addition to diagnosing or confirming the predisposition to PCa or BrCa, the methods and compositions described herein also provide a means of optimizing the treatment of a subject having such a disorder. Provided herein is a theranostic approach to treating and preventing PCa or BrCa, by integrating diagnostics and therapeutics to improve the real-time treatment of a subject. Practically, this means creating tests that can identify which patients are most suited to a particular therapy, and providing feedback on how well a drug is working to optimize treatment regimens.

Within the clinical trial setting, a theranostic method or composition of the invention can provide key information to optimize trial design, monitor efficacy, and enhance drug safety. For instance, "trial design" theranostics can be used for patient stratification, determination of patient eligibility (inclusion/exclusion), creation of homogeneous treatment groups, and selection of patient samples that are representative of the general population. Such theranostic tests can therefore provide the means for patient efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

The methods described herein can include retrospective analysis of clinical trial data as well, both at the subject level and for the entire trial, to detect correlations between a genetic profile as described herein and any measurable or quantifiable parameter relating to the outcome of the treatment, e.g., efficacy (the results of which may be binary (i.e., yes and no) as well as along a continuum), side-effect profile, recurrence, metastasis, hospitalizations, total healthcare cost, and/or dose response curves. The results of these correlations can then be used to influence decision-making, e.g., regarding treatment or therapeutic strategies, provision of services, and/or payment. For example, a correlation between a positive outcome parameter (e.g., high efficacy, low side effect profile, low recurrence, low metastasis, low total healthcare cost, and/or acceptable dose response curves) and a selected genetic profile can influence treatment such that the treatment is recommended or selected for a subject having the selected genetic profile.

Kits

Also within the scope of the invention are kits comprising a probe that hybridizes with a region of human chromosome as described herein and can be used to detect a polymorphism described herein. The kit can include one or more other elements including: instructions for use; and other reagents, e.g., a label, or an agent useful for attaching a label to the probe. Instructions for use can include instructions for diagnostic applications of the probe for assessing risk of PCa or BrCa in a method described herein. Other instructions can include instructions for attaching a label to the probe, instructions for performing in situ analysis with the probe, and/or instructions for obtaining a sample to be analyzed from a subject. As discussed above, the kit can include a label, e.g., any of the labels described herein. In some embodiments, the kit includes a labeled probe that hybridizes to a region of human chromosome as described herein, e.g., a labeled probe as described herein.

The kit can also include one or more additional probes that hybridize to and detect other genetic variants associated with risk for PCa or BrCa, e.g., as known in the art and described herein. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes.

Kits for use in self-testing can also be provided. For example, such test kits can include devices and instructions that a subject can use to obtain a sample, e.g., of buccal cells or blood, without the aid of a health care provider. For example, buccal cells can be obtained using a buccal swab or brush, or using mouthwash.

Kits as provided herein can also include a mailer, e.g., a postage paid envelope or mailing pack, that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms, e.g., the test requisition form, and the container holding the sample, can be coded, e.g., with a bar code, for identifying the subject who provided the sample.

Databases

Also provided herein are databases that include a list of polymorphisms as described herein, and wherein the list is largely or entirely limited to polymorphisms identified as useful in performing genetic diagnosis of or determination of susceptibility to PCa or BrCa as described herein. The list is stored, e.g., on a flat file or computer-readable medium. The databases can further include information regarding one or more subjects, e.g., whether a subject is affected or unaffected, clinical information such as endophenotype, age of onset of symptoms, any treatments administered and outcomes (e.g., data relevant to pharmacogenomics, diagnostics or theranostics), and other details, e.g., about the disorder in the subject, or environmental or other genetic factors. The databases can be used to detect correlations between a particular genetic profile and the information regarding the subject, e.g., to detect correlations between a genetic profile and a particular endophenotype, or treatment response.

Engineered Cells

Also provided herein are engineered cells that harbor one or more polymorphism described herein, e.g., one or more polymorphisms that constitute a genetic profile associated with PCa or BrCa. Such cells are useful for studying the effect of a polymorphism on physiological function, and for identifying and/or evaluating potential therapeutic agents for the treatment of PCa or BrCa, e.g., anti-cancer agents.

As one example, includes cells harboring one or more of the variant angiogenesis-associated alleles described herein Methods are known in the art for generating cells possessing altered sequence variants, such as homologous recombination between the endogenous gene and exogenous DNA molecule that is introduced into a cell (e.g., a cell of an animal). In some embodiments, the cells can be used to generate transgenic animals using well established methods.

The cells are preferably mammalian cells, e.g., neuronal type cells, in which an endogenous gene has been altered to include a polymorphism as described herein. Techniques such as targeted homologous recombination, can be used to insert the heterologous DNA, e.g., as described in Chappel, U.S. Pat. No. 5,272,071; and WO 91/06667.

EXAMPLES

The invention is further described in the following examples, which do not limit the scope of the invention described in the claims.

Example 1. Chemokine SNPs in Men of European Descent

To clarify the impact of sequence variants in chemokines and their corresponding receptors in relation to PCa, the current study used SNP profile data collected from 2277 European participants of the Cancer Genetic Markers of Susceptibility (CGEMS) project (688 aggressive cases, 488 non-aggressive cases, 1101 controls). For this analysis, the independent and joint modifying effects of 78 chemokine-associated SNPs were considered in relation to prostate and breast cancer outcomes, e.g., in relation to PCA risk and disease progression/aggressiveness.

Statistical Design

Comparisons of the frequency distribution of genotypes between cases and controls were performed with the chi-square test of heterogeneity.

Risk estimates associated with inheritance of at least one minor innate immunity sequence variant allele were expressed as odds ratios (ORs) and corresponding 95% Confidence Intervals (95% CI) using unconditional multivariate LR models, adjusted for potential confounders (e.g., age, family history of PCa or BCa).

All chi-square tests, permutation testing, and LR analyses were conducted using SAS 9.2 and Golden Helix SVS 7.0. Statistical significance was assessed using a P-value <0.05. Permutation testing p-values were calculated to adjust for multiple comparisons issues.

MDR was used to evaluate the individual and joint modifying effects of innate immunity SNPs in relation to PCa risk and aggressive tumor grade (on the internet at epistasis.org/).

This data-mining tool detects main and joint effects with 80% statistical power when given ≥200 cases and ≥200 controls.

Multi-locus genotypes were pooled into high-risk and low-risk groups, reducing high-dimensional data to a single dimension.

One-dimensional multi-locus genotype variable was evaluated for its ability to classify and predict disease susceptibility through cross-validation and permutation testing.

The results are shown below in Tables 1-3.

TABLE 1

Chemokine-associated SNPs and Prostate Cancer Risk among EA men

| Gene dbSNP ID Location Predicted Function† | Genotype | Cases N (%) | Controls N (%) | Adj OR (95% CI)‡ | p value | p value for trend | Permutation p-value |
|---|---|---|---|---|---|---|---|
| CCL16 | AA | 623 (53.0) | 563 (51.1) | 1.00 (reference) | 0.043 | 0.889 | 0.943 |
| rs2063979 | AG | 449 (38.2) | 465 (42.2) | 0.88 (0.74-1.05) | 0.122 | | |
| 3' UTR | GG | 104 (8.8) | 73 (6.7) | 1.30 (0.95-1.80) | 0.122 | | |
| mRNA splice site | ≥1 G allele | 553 (47.0) | 538 (48.9) | 0.94 (0.79-1.10) | 0.38 | | 1 |
| (ESE, ESS) miRNA | GG vs (AA + AG) | | | 1.38 (1.01-1.89) | 0.049 | | 0.969 |
| CCL21 | AA | 539 (45.8) | 456 (41.4) | 1.00 (reference) | 0.101 | 0.044 | 1 |
| rs2812377 | AC | 526 (44.7) | 529 (48.1) | 0.84 (0.71-1.00) | 0.051 | | |
| 5' near | CC | 111 (9.5) | 116 (10.5) | 0.82 (0.61-1.09) | 0.151 | | |
| TFBS gene | ≥1 C allele | 637 (54.2) | 645 (58.6) | 0.84 (0.71-0.99) | 0.034 | | 0.91 |
| | CC vs (AA + AC) | | | 0.84 (0.68-1.78) | 0.382 | | 1 |
| CCR4 | CC | 523 (44.5) | 548 (49.8) | 1.00 (reference) | 0.033 | 0.045 | 0.891 |
| rs2228428 | CT | 535 (45.5) | 445 (40.4) | 1.28 (1.07-1.52) | 0.009 | | |
| Exon 1 | TT | 118 (10.0) | 108 (9.8) | 1.13 (0.85-1.51) | 0.356 | | |
| Tyr338Tyr | ≥1 T allele | 653 (55.5) | 553 (50.2) | 1.25 (1.06-1.47) | 0.011 | | 0.533 |
| | TT vs (CC + CT) | | | 1.01 (0.76-1.33) | 0.858 | | 1 |
| CX3CL11 | TT | 710 (60.4) | 701 (63.7) | 1.00 (reference) | 0.077 | 0.037 | 0.996 |
| rs4151117 | TG | 390 (33.1) | 350 (31.8) | 1.10 (0.92-1.32) | 0.294 | | |
| 3' UTR | GG | 76 (6.5) | 50 (4.5) | 1.56 (1.07-2.26) | 0.032 | | |
| miRNA | ≥1 G allele | 466 (39.6) | 400 (36.3) | 1.16 (0.98-1.38) | 0.106 | | 1 |
| | GG vs (TT + TG) | | | 1.50 (1.04-2.17) | 0.046 | | 0.959 |
| IFNGR2 | GG | 423 (36.0) | 382 (34.7) | 1.00 (reference) | 0.065 | 0.092 | |
| rs2284553 | GA | 579 (49.2) | 516 (46.9) | 1.01 (0.84-1.21) | 0.887 | | |
| Intron 1 | AA | 174 (14.8) | 203 (18.4) | 0.77 (0.60-0.98) | 0.041 | | |
| | ≥1 A Allele | 753 (64.0) | 719 (65.3) | 0.94 (0.79-1.12) | 0.525 | | |
| | AA vs (GG + GA) | | | 0.77 (0.61-0.96) | 0.02 | | |

TABLE 1-continued

Chemokine-associated SNPs and Prostate Cancer Risk among EA men

| Gene dbSNP ID Location Predicted Function† | Genotype | Cases N (%) | Controls N (%) | Adj OR (95% CI)‡ | p value | p value for trend | Permutation p-value |
|---|---|---|---|---|---|---|---|
| CCL17 | CC | 483 (41.1) | 496 (45.0) | 1.00 (reference) | 0.081 | 0.025 | 0.996 |
| rs223895 | CT | 548 (46.6) | 494 (44.9) | 1.15 (0.97-1.38) | 0.144 | | |
| Intron 1 | TT | 145 (12.3) | 111 (10.1) | 1.38 (1.04-1.82) | 0.038 | | |
| | ≥1 T allele | 693 (58.9) | 605 (55.0) | 1.20 (1.01-1.41) | 0.055 | | 0.973 |
| | TT vs (CC + CT) | | | 1.28 (0.98-1.66) | 0.09 | | 0.997 |
| PIAS1 | GG | 912 (77.6) | 897 (81.5) | 1.00 (reference) | 0.068 | 0.022 | 0.993 |
| rs16951657 | GT | 253 (21.5) | 196 (17.8) | 1.27 (1.03-1.56) | 0.024 | | |
| 3' near gene | TT | 11 (0.9) | 8 (0.7) | 1.44 (0.57-3.58) | 0.518 | | |
| | ≥1T allele | 264 (22.4) | 204 (18.5) | 1.28 (1.04-1.57) | 0.021 | | 0.764 |
| | TT vs (GG + GT) | | | 1.37 (0.55-3.42) | 0.585 | | 1 |

†Exonic splicing enhancer (ESE) or exonic splicing silencer (ESS) binding sites; MicroRNAs (miRNA) are 21-23 base single stranded RNAs that bind to the end of mRNA and can inhibit protein translation. Human miRNA is usually complementary to the 3'UTR region of an mRNA; Transcription factor binding site (TFBS).
‡Risk Estimates are adjusted for age and family history of disease.

TABLE 2

Chemokine-Related SNPs and Aggressive PCa among EA men.

| Gene dbSNP ID Location Predicted Function† | Genotype | Non aggressive n (%) | Aggressive n (%) | Adjusted OR (95% CI) | p-value | p trend | permutation p-value |
|---|---|---|---|---|---|---|---|
| CCL4 | GG | 423 (61.5) | 275 (56.4) | 1.00 (referent) | 0.0476 | 0.3124 | 0.972 |
| rs1719147 | GA | 222 (32.3) | 190 (38.9) | 0.76 (0.60-0.98) | 0.0286 | | |
| Intron 2 | AA | 43 (6.2) | 23 (4.7) | 1.19 (0.70-2.03) | 0.4694 | | |
| TFBS | ≥1 A allele | 265 (38.5) | 213 (43.6) | 0.81 (0.64-1.02) | 0.0778 | | 0.996 |
| | AA vs (GG + GA) | | | 1.32 (0.78-2.23) | 0.2607 | | 1 |
| CCL16 | GG | 414 (60.2) | 309 (63.3) | 1.00 (referent) | 0.0818 | 0.0922 | 0.999 |
| rs854680 | GT | 238 (34.6) | 166 (34.0) | 1.08 (0.84-1.38) | 0.5908 | | |
| 5' near gene | TT | 36 (5.2) | 13 (2.7) | 2.10 (1.09-4.02) | 0.029 | | |
| TFBS | ≥1 T allele | 274 (39.8) | 179 (36.7) | 1.16 (0.91-1.47) | 0.2749 | | 1 |
| | TT vs (GG + GT) | | | 2.04 (1.07-3.89) | 0.0331 | | 0.834 |
| CCL16 | AA | 347 (50.4) | 276 (56.6) | 1.00 (referent) | 0.1147 | 0.0494 | 1 |
| rs2063979 | AG | 276 (40.1) | 173 (35.4) | 1.28 (1.00-1.64) | 0.059 | | |
| 3' UTR | GG | 65 (9.5) | 39 (8.0) | 1.36 (0.88-2.08) | 0.196 | | |
| Splicing (ESE, ESS) miRNA | ≥1 G allele | 341 (49.6) | 212 (43.4) | 1.30 (1.02-1.64) | 0.0384 | | 0.939 |
| | GG vs (AA + AG) | | | 1.22 (0.81-1.86) | 0.3868 | | 1 |
| CCL18 | GG | 342 (49.7) | 218 (44.7) | 1.00 (referent) | 0.1028 | 0.0373 | 1 |
| rs14304 | GA | 294 (42.7) | 219 (44.9) | 0.84 (0.66-1.08) | 0.2104 | | |
| 3' UTR | AA | 52 (7.6) | 51 (10.4) | 0.64 (0.42-0.98) | 0.0453 | | |
| miRNA | ≥1 A allele | 346 (50.3) | 270 (55.3) | 0.81 (0.64-1.02) | 0.088 | | 0.998 |
| | AA vs (GG + GA) | | | 0.70 (0.47-1.04) | 0.0851 | | 0.998 |
| CCL28 | CC | 467 (67.9) | 319 (65.4) | 1.00 (referent) | 0.013 | 0.9834 | 0.574 |
| rs779850 | CT | 192 (27.9) | 161 (33.0) | 0.81 (0.63-1.04) | 0.112 | | |
| Intron 2 | TT | 29 (4.2) | 8 (1.6) | 2.50 (1.12-5.56) | 0.0255 | | |
| | ≥1 T allele | 221 (32.1) | 169 (34.6) | 0.89 (0.70-1.14) | 0.368 | | 1 |
| | TT vs (CC + CT) | | | 2.66 (1.21-5.91) | 0.0162 | | 0.531 |
| CCR4 | CC | 553 (80.4) | 412 (84.4) | 1.00 (referent) | 0.082 | 0.161 | 0.999 |
| rs6770096 | CT | 129 (18.8) | 69 (14.2) | 1.41 (1.03-1.94) | 0.0417 | | |
| 3' near gene | TT | 6 (0.8) | 7 (1.4) | 0.62 (0.21-1.87) | 0.4233 | | |
| | ≥1 T allele | 135 (19.6) | 76 (15.6) | 1.34 (0.98-1.82) | 0.075 | | 0.996 |
| | TT vs (CC + CT) | | | 0.59 (0.20-1.76) | 0.368 | | 1 |
| IFNG | AA | 603 (87.6) | 446 (91.4) | 1.00 (referent) | 0.0413 | | 0.951 |
| rs2069716 intron 3 | AG + GG | 85 (12.4) | 42 (8.6) | 1.52 (1.03-2.25) | | | |
| XCL1 | CC | 264 (38.4) | 153 (31.3) | 1.00 (reference) | 0.014 | 0.004 | 0.597 |
| rs2300295 | CA | 326 (47.4) | 241 (49.4) | 0.78 (0.60-1.01) | 0.0661 | | |
| intron 1 | AA | 98 (14.2) | 94 (19.3) | 0.60 (0.42-0.85) | 0.0043 | | |
| TFBS | ≥1 A allele | 424 (61.6) | 335 (68.7) | 0.73 (0.57-0.93) | 0.0133 | | 0.61 |
| | AA vs (CC + CA) | | | 0.70 (0.51-0.95) | 0.0222 | | 0.735 |

TABLE 3

Chemokine-Related Sequence Variants and BrCA among EA women.

| Gene | Genotype | Cases N (%) | Controls N (%) | OR (95% CI)‡ | p value | p-value for trend | Permutation p-value |
|---|---|---|---|---|---|---|---|
| CCL16 | AA | 552 (48.4) | 564 (49.6) | 1.00 (Referent) | 0.007 | 0.46 | 0.366 |
| rs2063979 | AG | 455 (44.5) | 455 (40.0) | 1.13 (0.95, 1.35) | 0.129 | | |
| 3' UTR | GG | 118 (10.4) | 118 (10.4) | 0.70 (0.52, 0.95) | 0.024 | | |
| Splicing | ≥1 G allele | | | 1.04 (0.88, 1.23) | 0.558 | | 1 |
| (ESE, ESS, Abolish Domain); miRNA | GG vs (AA + AG) | 573 (50.4) | 573 (50.4) | 0.66 (0.49, 0.89) | 0.006 | | 0.285 |
| CCL17 | CC | 517 (45.3) | 517 (45.3) | 1.00 (Referent) | 0.059 | 0.984 | 0.984 |
| rs223895 | CT | 481 (42.1) | 481 (42.1) | 1.24 (1.04, 1.47) | 0.019 | | |
| Intron 1 | TT | 144 (12.6) | 144 (12.6) | 1.07 (0.82, 1.40) | 0.685 | | |
| | ≥1 T allele | | | 1.20 (1.01, 1.41) | 0.038 | 0.916 | 0.916 |
| | TT vs (CC + CT) | 676 (59.0) | 625 (54.7) | 0.96 (0.75, 1.24) | 0.685 | 1 | 1 |
| CCL23 | AA | 762 (66.7) | 731 (64.1) | 1.00 (Referent) | 0.092 | 0.072 | 1 |
| rs854656 | AC | 348 (30.5) | 359 (31.5) | 0.93 (0.78, 1.10) | 0.408 | | |
| TFBS | CC | 32 (33.3) | 50 (4.4) | 0.89 (0.75, 1.06) | 0.418 | | |
| | ≥1 C allele | | | 0.61 (0.39, 0.96) | 0.192 | | 1 |
| | CC vs (AA + AC) | 380 (33.3) | 409 (35.9) | 0.63 (0.40, 0.99) | 0.044 | | 0.939 |
| CCR8 | CC | 543 (47.4) | 546 (47.8) | 1.00 (Referent) | 0.073 | 0.257 | 0.994 |
| rs12107527 | CT | 482 (42.1) | 507 (44.4) | 0.96 (0.81, 1.14) | 0.061 | | |
| TFBS | TT | 120 (10.5) | 89 (7.8) | 1.36 (1.01, 1.84) | 0.046 | | |
| | ≥1 T allele | | | 1.02 (0.86, 1.20) | 0.853 | | 1 |
| | TT vs (CC + CT) | 602 (52.6) | 596 (52.2) | 1.39 (1.04, 1.85) | 0.026 | | 0.834 |
| CXCL16 | CC | 939 (82.3) | 982 (86.3) | 1.00 (Referent) | 0.032 | 0.012 | 0.895 |
| rs2304973 | CT | 191 (16.7) | 147 (12.9) | 1.36 (1.08, 1.72) | 0.01 | | |
| TFBS | TT | 11 (1.0) | 9 (0.8) | 1.26 (0.52, 3.07) | 0.587 | | |
| | ≥1 T allele | | 156 (13.7) | 1.36 (1.08, 1.70) | 0.009 | | 0.445 |
| | TT vs (CC + CT) | 202 (17.7) | | 1.21 (0.50, 2.93) | 0.659 | | 1 |
| IFNGR2 | GG | 616 (53.8) | 546 (47.8) | 1.00 (Referent) | 0.0116 | 0.014* | 0.676 |
| rs8131980 | GA | 417 (36.4) | 474 (41.5) | 0.78 (0.66, 0.93) | 0.005 | | |
| 3' near gene | AA | 112 (9.8) | 122 (10.7) | 0.81 (0.6, 1.07) | 0.151 | | |
| | ≥1 A allele | 529 (46.2) | 596 (52.2) | 0.79 (0.67, 0.93) | 0.004 | | 0.241 |
| | AA vs (GG + GA) | | | 0.90 (0.69, 1.18) | 0.477 | | 1 |

TABLE 4

Main and Joint Effects in Relation to BrCA Risk using MDR after SurfNTurf Filtering

| Best Model | # Combinations | CVC | Accuracy | P-Value |
|---|---|---|---|---|
| One Factor IFNGR2_rs8131980 | 57 | 9/10 | 0.5259 | 0.1570 |
| Two Factor IFNGR2_rs8131980 CCR4_rs228428 | 1576 | 10/10 | 0.5427 | 0.0165 |
| Three Factor IFNGR2_rs8131980 CCR4_rs228428 CCL8_rs3138036 | 29620 | 2/10 | 0.4970 | 0.156 |
| Four Factor IFNGR2_rs8131980 CCR4_rs228428 CCL8_rs3138036 XCL1_rs2300295 | 395010 | 3/10 | 0.5026 | 0.413 |

These results indicate that the inheritance of the CCL16_rs2063979 "GG" (under the recessive genetic model), CCR4_rs2228428 "CT" or "CT+TT", CX3CL1_rs4151117 "GG", CCL17_rs223895 "TT", or PIAS1_rs16951657 "GT" or "GT+TT" was associated with an 1.25 to 1.56-fold increase in the risk of developing PCA (p≤0.049). In contrast, possession at least one minor CCL21_rs2812377 "C" allele or the IFNGR2_rs2284553 "AA" genotype was linked to a marginal 16 to 23% decrease in risk (p≤0.041). With respect to disease aggressiveness, inheritance the CCL4 rs1719147 "GA", CCL18_rs14304 "GA" or XCL1_rs2300295 "AA" genotypes were related to a 36-40% reduction in aggressive PCA (p≤0.045), relative to those with the referent genotype. In contrast, inheritance of the CCL16 rs854680 "TT", CCL16 rs2063979 "AG+GG", CCL28 rs779850 "TT", CCR4 rs6770096 "CT", IFNG rs2069716 "AG+GG" genotypes were linked to a 1.41-2.50 fold increase in the risk of developing aggressive prostate cancer.

In addition, possession of the CCL16_rs2063979 "GG" (under the recessive genetic model), CCL23 rs854656 "GG" (under the recessive genetic model), or IFNGR2 rs8131980 "GA+AA" genotypes was linked with a 21-37% reduction in BrCa risk after adjusting for age. Inheritance of the CCL17 rs223895 "CT+TT", CCR8 rs12107527 "TT" (under the recessive genetic model), or the CXCL16 rs2304973 "TT" (under the recessive genetic model) genotypes were associated with a 20-39% increase in the risk of developing BrCa.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising:
   obtaining a blood sample comprising DNA from a subject who is suspected of being at risk of developing prostate cancer (PCa);
   contacting the sample with oligonucleotide probes that are identical to at least 20 nucleotides of SEQ ID NO:6 and that terminate adjacent to the polymorphic site or encompass the polymorphic site at rs2063979 and detecting the genotype at rs2063979;
   contacting the sample with oligonucleotide probes that are identical to at least 20 nucleotides of SEQ ID NO:8 and that terminate adjacent to the polymorphic site or encompass the polymorphic site at rs2228428 and detecting the genotype at rs2228428;
   contacting the sample with oligonucleotide probes that are identical to at least 20 nucleotides of SEQ ID NO: 15 and that terminate adjacent to the polymorphic site or encompass the polymorphic site at rs4151117 and detecting the genotype at rs4151117;
   contacting the sample with oligonucleotide probes that are identical to at least 20 nucleotides of SEQ ID NO:9 and that terminate adjacent to the polymorphic site or encompass the polymorphic site at rs223895 and detecting the genotype at rs223895;
   contacting the sample with oligonucleotide probes that are identical to at least 20 nucleotides of SEQ ID NO:4 and that terminate adjacent to the polymorphic site or encompass the polymorphic site at rs16951657 and detecting the genotype at rs16951657; and
   detecting levels of Prostate Serum Antigen (PSA) in a blood sample from the subject with a "GG" genotype at rs2063979, a "CT" genotype at rs2228428, a "GG" genotype at rs4151117, a "TT" genotype at rs223895, or at least one "T" allele at rs16951657.

2. The method of claim 1, wherein the subject is a patient having one or more risk factors associated with PCa.

3. The method of claim 2, wherein the risk factors associated with PCa include one or more of: age; race/ethnicity; nationality; family history; diet; obesity; lack of exercise; inflammation of the prostate; infection; and vasectomy.

4. The method of claim 1, wherein the subject has one or more of a grandparent, parent, uncle, sibling, or child who has or had PCa.

5. The method of claim 1 further comprising performing an imaging study on the selected subject to detect the development of PCa or performing a prostate biopsy on the selected subject to detect cancerous cells.

6. The method of claim 1 further comprising administering a prophylactic treatment to the selected subject to decrease their risk of developing PCa.

7. The method of claim 1 further comprising administering a treatment for PCa to the selected subject.

8. The method of claim 7, wherein the treatment is surgery; radiation therapy; or hormone therapy.

9. The method of claim 1, wherein detecting the genotype comprises sequencing.

10. The method of claim 1, wherein detecting the genotype comprises performing fluorescence polarization template-directed dye-terminator incorporation.

11. The method of claim 1, wherein the probes are labeled.

* * * * *

UNITED STATES PATENT AND TRADEMARK OFFICE
CERTIFICATE OF CORRECTION

PATENT NO. : 9,879,324 B2
APPLICATION NO. : 14/009197
DATED : January 30, 2018
INVENTOR(S) : La Creis Renee Kidd and Kevin Sean Kimbro It is certified that error appears in the above-identified patent and that said Letters Patent is hereby corrected as shown below:

On the Title Page

Item (73) (Assignees), Line 2, delete "Fondation," and insert -- Foundation --

Signed and Sealed this
Eleventh Day of September, 2018

Andrei Iancu
*Director of the United States Patent and Trademark Office*